(12) United States Patent
Gurumoorthy et al.

(10) Patent No.: US 9,704,176 B2
(45) Date of Patent: *Jul. 11, 2017

(54) METHODS AND APPARATUS TO DETERMINE EFFICIENCIES OF MEDIA DELIVERY ACROSS PLATFORMS

(71) Applicant: The Nielsen Company (US), LLC, New York, NY (US)

(72) Inventors: Ramachandran Gurumoorthy, Berkeley, CA (US); Robert T. Knight, Berkeley, CA (US)

(73) Assignee: The Nielsen Company (US), LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/365,157

(22) Filed: Nov. 30, 2016

(65) Prior Publication Data
US 2017/0083934 A1 Mar. 23, 2017

Related U.S. Application Data

(63) Continuation of application No. 13/837,148, filed on Mar. 15, 2013, now Pat. No. 9,552,589.

(51) Int. Cl.
*G06Q 30/02* (2012.01)
*A61B 5/0476* (2006.01)
*A61B 3/113* (2006.01)

(52) U.S. Cl.
CPC .......... *G06Q 30/0243* (2013.01); *A61B 3/113* (2013.01); *A61B 5/0476* (2013.01);
(Continued)

(58) Field of Classification Search
CPC ............... G06Q 30/02; G06Q 30/0203; G06Q 30/0242; G06Q 30/0243
See application file for complete search history.

(56) References Cited

U.S. PATENT DOCUMENTS 5,675,510 A * 10/1997 Coffey ................ G06F 11/3466
707/999.104
6,099,319 A * 8/2000 Zaltman .................. A61B 5/16
434/236

(Continued)

*Primary Examiner* — David Stoltenberg
*Assistant Examiner* — Shawn Lillemo
(74) *Attorney, Agent, or Firm* — Hanley, Flight & Zimmerman, LLC

(57) ABSTRACT

Methods and apparatus to determine efficiencies of media delivery across platforms are disclosed. An example method includes measuring, with a sensor, first neuro-response data from a person when exposed to media output via a first media delivery platform type. Measuring second neuro-response data from the person when exposed to media output via a second media delivery platform type, different than the first media delivery platform type. Accessing a first and second performance metric for the respective media delivery platform type, the performance metrics based on a first and second reach of the respective media delivery platform types with respect to a target group of audience members. Accessing a first and second effectiveness metric for the respective media delivery platform types, the effectiveness metric based on the respective neuro-response data. Rating at least one of the first or second media delivery platform types based on the first and the second platform metrics.

20 Claims, 9 Drawing Sheets

(52) U.S. Cl.
CPC ... *A61B 2503/12* (2013.01); *A61B 2562/0219* (2013.01); *G06Q 30/0245* (2013.01); *G06Q 30/0246* (2013.01); *G06Q 30/0251* (2013.01)

(56) References Cited

U.S. PATENT DOCUMENTS

| | | | | |
|---|---|---|---|---|
| 6,108,637 | A * | 8/2000 | Blumenau | G06F 11/34 705/30 |
| 6,327,619 | B1 * | 12/2001 | Blumenau | G06F 17/30876 705/14.73 |
| 7,895,075 | B2 * | 2/2011 | Gettys | G06Q 30/02 705/14.41 |
| 8,321,273 | B2 * | 11/2012 | Briggs | G06Q 30/02 705/14.41 |
| 2008/0221400 | A1 * | 9/2008 | Lee | A61B 5/024 600/301 |
| 2008/0243573 | A1 * | 10/2008 | Nasser | G01S 19/09 705/7.31 |
| 2009/0018996 | A1 * | 1/2009 | Hunt | G06Q 30/02 |
| 2009/0150217 | A1 * | 6/2009 | Luff | G06Q 30/02 705/7.32 |
| 2011/0035276 | A1 * | 2/2011 | Ghosh | G06Q 30/02 705/14.46 |
| 2011/0119124 | A1 * | 5/2011 | Pradeep | G06Q 30/02 705/14.42 |
| 2014/0244345 | A1 * | 8/2014 | Sollis | G06Q 30/02 705/7.29 |

\* cited by examiner

| PLATFORM | SUBPLATFORM | GROUP | PERF | COST ($) | PERF/$ |
|---|---|---|---|---|---|
| Television | ABC Networks | M24 | 339122 | 100000 | 3.391 |
| | | M35 | 350168 | 100000 | 3.502 |
| | CBS Networks | M24 | 624098 | 120000 | 5.201 |
| | | M35 | 461350 | 120000 | 3.845 |
| | NBC Networks | M24 | 250842 | 150000 | 1.672 |
| | | M35 | 58446 | 150000 | 0.390 |
| | CNN | M24 | 315994 | 200000 | 1.580 |
| | | M35 | 412789 | 200000 | 2.064 |
| Total TV | | 314 → | 2812808 | 1140000 | 2.467 |
| Online | www.youtube.com | M24 | 969019 | 100000 | 9.690 |
| | | M35 | 218427 | 100000 | 2.184 |
| | www.hulu.com | M24 | 196720 | 100000 | 1.967 |
| | | M35 | 296949 | 100000 | 2.969 |
| | Product Site | M24 | 262762 | 120000 | 2.190 |
| | | M35 | 214082 | 120000 | 1.784 |
| Total Online | | 314 → | 2157958 | 640000 | 3.372 |
| Mobile | iPhone app | M24 | 193120 | 50000 | 3.862 |
| | | M35 | 111489 | 50000 | 2.230 |
| | Android app | M24 | 99232 | 45000 | 2.205 |
| | | M35 | 250095 | 45000 | 5.558 |
| | Blackberry app | M24 | 2560 | 30000 | 0.085 |
| | | M35 | 205390 | 30000 | 6.846 |
| Total Mobile | | 314 → | 861885 | 250000 | 3.448 |
| Outdoor | Times Square | M24 | 140094 | 300000 | 0.467 |
| | | M35 | 248548 | 300000 | 0.828 |
| | Flying Banner | M24 | 9773 | 10000 | 0.977 |
| | | M35 | 44797 | 10000 | 4.480 |
| | Naming Rights | M24 | 321971 | 500000 | 0.644 |
| | | M35 | 216328 | 500000 | 0.433 |
| Total Outdoor | | 314 → | 981512 | 810000 | 1.212 |
| Total Campaign | | | 6814163 | 1420000 | 4.799 |

FIG. 4

METHODS AND APPARATUS TO DETERMINE EFFICIENCIES OF MEDIA DELIVERY ACROSS PLATFORMS

CROSS REFERENCE TO RELATED APPLICATIONS

This patent arises from a continuation of U.S. patent application Ser. No. 13/837,148, filed Mar. 15, 2013, entitled "Methods And Apparatus To Determine Efficiencies Of Media Delivery Across Platforms," now U.S. Pat. No. 9,552,589. The U.S. patent application Ser. No. 13/837,148 is hereby incorporated herein by reference in its entirety

FIELD OF THE DISCLOSURE

This disclosure relates generally to media delivery and, more particularly, to methods and apparatus to determine efficiencies of media delivery across platforms.

BACKGROUND

Media delivery, such as the presentation of programs and advertisements, has expanded from platforms such as stationary television and stationary radio to online (e.g., Internet-based) and mobile (e.g., cell phone or other portable device) delivery. Different platforms are accessed by different numbers and demographics of individuals.

BRIEF DESCRIPTION OF THE DRAWINGS

FIG. 4 is a table illustrating example calculations of cost effectiveness of a media campaign for multiple platforms.

Wherever possible, the same reference numbers will be used throughout the drawing(s) and accompanying written description to refer to the same or like parts.

DETAILED DESCRIPTION

Figure 1:
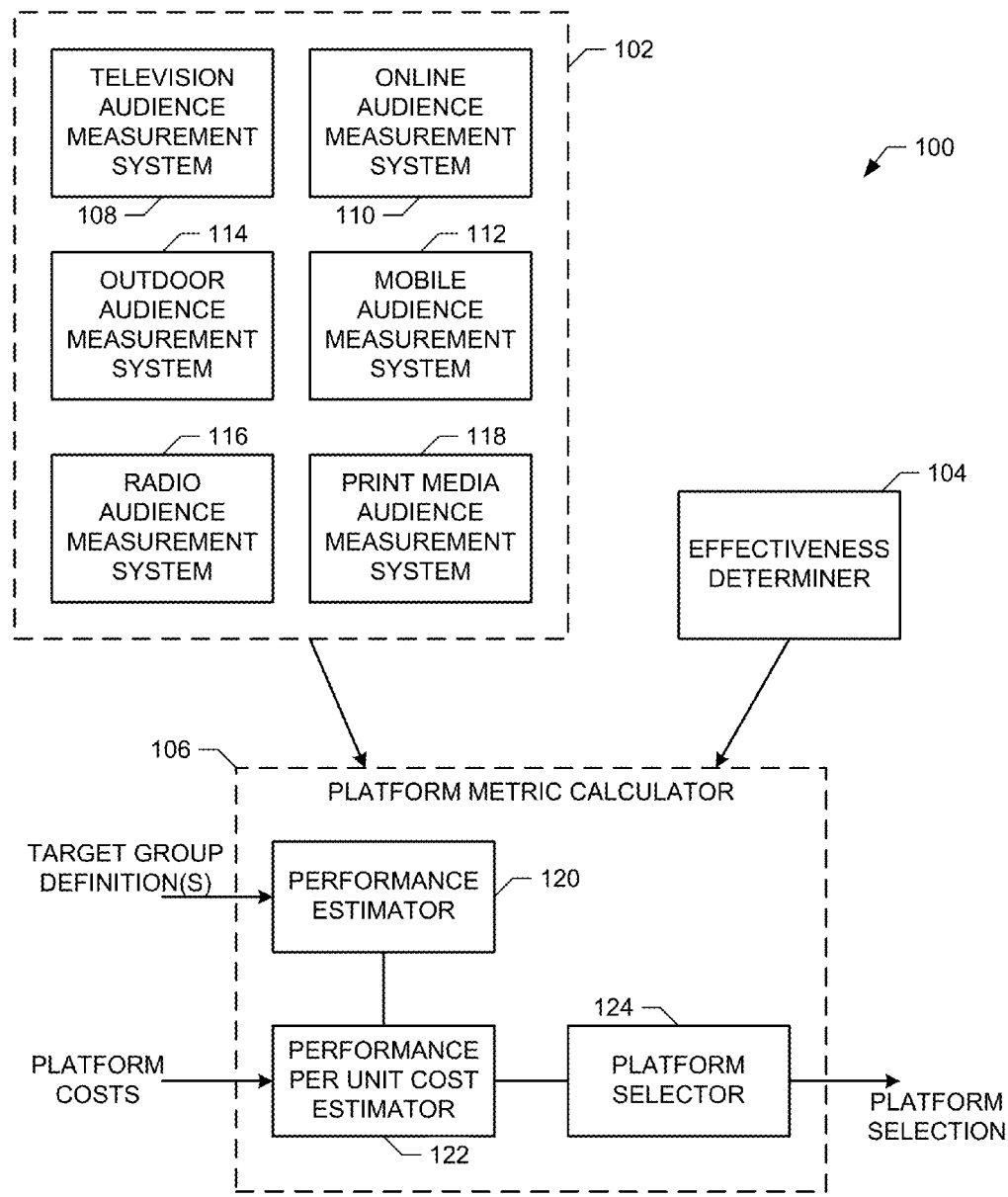
FIG. 1 is a block diagram of an example system constructed in accordance with the teachings of this disclosure to determine an effectiveness of a multi-platform media campaign.

Audience measurement providers, such as The Nielsen Company, measure audience reach and calculate ratings based on multiple platforms (e.g., television, radio, mobile, online, outdoor, print media, etc.). Each media platform (e.g., television, radio, mobile, online, outdoor, print media, etc.) has norms (e.g., baselines of scores and/or ratings for specific types of media (e.g., content and/or advertisements). Such norms are actionable thresholds of success. For example, television ratings have specific baselines, by demography and/or genre of content, for what is considered a good, successful, and/or popular show. Advertisers desire to understand the cumulative effects and the relative impacts of media campaigns (e.g., advertising, programming) when a campaign is launched that uses one or more media platforms. For example, advertisers may desire to know whether one platform is more influential than another platform for a given campaign.

While TV ratings are a standardized currency in the television advertising market, platforms such as mobile and online ratings do not clearly relate to TV ratings using known measurements as a direct comparison. Furthermore, ratings based on different platforms may have different respective levels of granularity and/or quality, such as a level of noise in the data, comprehensiveness of normative comparisons, and/or reliability of market performance predictability on different platforms. For example, TV rating predictions are considered more reliable than predictions of online or mobile ratings. Thus, comparisons between these platforms are difficult.

Example methods and apparatus disclosed herein enable effective comparison and rationalization of performance (e.g., ratings) between different distribution platforms, such as television, radio, online, mobile, outdoor, and/or print media, among others. Comparison and/or rationalization enabled by example methods and apparatus disclosed herein provide a holistic view of the returns of a campaign across multiple platforms and can be used to adjust future media campaigns based on the performances for, for example, specific demographies and/or geographies on a platform-by-platform basis. Example methods and apparatus disclosed herein enable the use of cross-platform performance determinations and/or comparisons to improve (e.g., optimize) selection and/or spending across multiple platforms for a media campaign.

Example methods and apparatus disclosed herein determine neurological effectiveness or efficiency measurements for each platform, subplatform, and/or target group to be measured. Example effectiveness or efficiency measurements may be representative of persuasion, purchase intent, attention, emotion, memory, and/or fluency.

As used herein, the term "persuasion" refers to a medium's attempt to generate an intent to behave in a particular manner (e.g., to purchase a particular good or service). As used herein, the term "effectiveness" refers to an ability or propensity of media to achieve a desired effect in an individual (e.g., to create a lasting memory, to change a rate of media consumption, to influence a purchasing decision, etc.). As used herein, an "effectiveness metric" refers to a composite measure of cognitive processing (e.g., a weighted combination of attention, emotional engagement, and memory activation). As used herein, the term "engagement" or "emotional engagement" refers to a measure of intensity of emotional response and/or automatic motivational classification of stimuli (e.g., non-conscious classification of sensory experiences as potentially rewarding (approach motivation) or potentially threatening (avoidance motivation)). As used herein, the term "attention" refers to a measure of sustained focus and/or shifts in focus over time. As used herein, the term "fluency" refers to a measure of an audience member's ability to understand the media to which he or she is exposed. As used herein, the term "reach" refers to the unduplicated audience of one or more media platforms. As used herein, the term "performance metric" is a measure of any result of interest associated with media, a platform, or a combination of media on a platform. In some examples disclosed herein, a media impact performance metric is a product of an effectiveness measurement and a reach measurement. As used herein, the term "subplatform" refers to a subset of media presentation types that can occur and be classified as occurring on a platform. As used herein, the term "platform" is generic to platforms and subplatforms. As used herein, the term "target group" refers to a group of people of interest who share at least one characteristic, such as age, gender, or income range.

As used herein, the efficiency, effectiveness, and/or performance metrics, may be measures corresponding to specific media when delivered via a specific platform (and/or subplatform). Additionally or alternatively, the efficiency, effectiveness, and/or performance metrics may be measures for a corresponding platform (and/or subplatform) without reference to any particular media. For example, the efficiency, effectiveness, and/or performance of a plurality of media delivered via a platform (and/or subplatform) may be generalized to the platform (and/or subplatform).

Example methods and apparatus disclosed herein obtain reach measurements for TV, online, mobile, and/or other platforms of interest. Example methods and apparatus disclosed herein combine respective effectiveness measurements and reach measurements for each platform to obtain an estimated media impact performance metric of the platform. Some example methods and apparatus determine a product (e.g., multiplication) of the effectiveness metric with the reach to determine the media impact performance metric. In some examples, in addition to platform metrics (e.g., performance metrics for a platform as a whole), performance metrics are determined for subplatforms and/or target groups on a platform or subplatform.

FIG. 1 is a block diagram of an example system 100 constructed in accordance with the teachings of this disclosure to determine an effectiveness of a multi-platform media campaign. The example system 100 of FIG. 1 includes an audience measurement system 102, an effectiveness determiner 104, and a platform metric calculator 106. The example audience measurement system 102 of FIG. 1 determines audience information, such as reach, for each of multiple media platforms (e.g., television, online, mobile devices, outdoor, radio, print media, etc.). Media platforms are also referred to herein as simply "platforms."

In some examples, the audience measurement system 102 of FIG. 1 determines the audience information for each of the example platforms by target group. Target groups may be defined based on one or a combination of age, gender, demographic group, socioeconomic status, geographic location, personal interests, size of household, and/or other criteria. Accordingly, a given target group (e.g., males, age 24-35) may overlap with some target groups (e.g., persons in a household with $60,000-$99,999 annual income, persons located on the east coast) while being mutually exclusive with other target groups (e.g., females, age 24-35, versus females, age 36-45).

The example audience measurement system 102 of FIG. 1 includes a television audience measurement system 108, an online audience measurement system 110, a mobile audience measurement system 112, an outdoor audience measurement system 114, a radio audience measurement system 116, and a print media audience measurement system 118. However, alternative and/or additional systems may be used. For example, more, fewer, and/or different systems may be employed.

The example television audience measurement system 108 of FIG. 1 determines reach for one or more target groups and/or for a total population. Additionally, the example television audience measurement system 108 determines reach for one or more subplatforms (e.g., local stations, broadcasting networks, cable and/or satellite channels, pay-per-view channels, time-shifted viewing, space-shifted viewing, etc.) of the television platform. The precise methodologies and/or structures of the television audience measurement system 108 of FIG. 1 are irrelevant to this disclosure. The example television audience measurement system 108 of FIG. 1 may be implemented, for example, according to any system or combination(s) of systems described in U.S. Pat. Nos. 5,481,294, 5,771,307, 5,550,928, 6,647,548, 7,239,981 7,640,141, and/or 8,359,610, all of which are hereby incorporated by reference in their entireties.

The example online audience measurement system 110 of FIG. 1 determines reach for one or more target groups and/or for a total population. Additionally, the example online audience measurement system 110 determines reach for one or more subplatforms (e.g., web sites, web pages, online services, streaming media providers, peer-to-peer networks, downloaded media, etc.) of the online platform. The precise methodologies and/or structures of the online audience measurement system 110 of FIG. 1 are irrelevant to this disclosure. The example online audience measurement system 110 may be implemented, for example, according to any system or combination(s) of systems described in U.S. Pat. Nos. 5,675,510, 6,108,637, and/or 6,327,619, all of which are hereby incorporated by reference in their entireties.

The example mobile audience measurement system 112 of FIG. 1 determines reach for one or more target groups and/or for a total population. Additionally, the example mobile audience measurement system 112 determines reach for one or more subplatforms (e.g., mobile network carriers, mobile handset manufacturers, mobile handset software providers, mobile handset models, mobile applications, etc.) of the mobile platform. The precise methodologies and/or structures of the mobile audience measurement system 112 of FIG. 1 are irrelevant to this disclosure. The example mobile audience measurement system 112 may be implemented, for example, according to any system or combination(s) of systems described in U.S. Pat. Nos. 5,675,510 and/or 6,108,637, and/or U.S. patent Pre-Grant Publication No. 2012/0151079, all of which are hereby incorporated by reference in their entireties.

The example outdoor audience measurement system 114 of FIG. 1 determines reach for one or more target groups and/or for a total population. Additionally, the example outdoor audience measurement system 114 determines reach for one or more subplatforms (e.g., billboards, locations, outdoor advertising companies and/or networks, mobile outdoor advertising such as advertising trucks, taxis, and/or airplane banners, etc.) of the outdoor platform. The precise methodologies and/or structures of the outdoor audience measurement system 114 of FIG. 1 are irrelevant to this disclosure. The example outdoor audience measurement system 114 may be implemented, for example, according to any system or combination(s) of systems described in U.S. patent Pre-Grant Publication No. 2008/0243573 and/or in U.S. patent application Ser. No. 13/793,771, filed on Mar. 11, 2013, and entitled "Methods and Apparatus to Measure Exposure to Mobile Advertisements," all which are hereby incorporated by reference in their entireties.

The example radio audience measurement system 116 of FIG. 1 determines reach for one or more target groups and/or for a total population. Additionally, the example radio audience measurement system 116 determines reach for one or more subplatforms (e.g., terrestrial broadcast radio, Internet radio, satellite radio, high definition radio, particular radio channels, particular radio networks, etc.) of the radio platform. The precise methodologies and/or structures of the radio audience measurement system 116 of FIG. 1 are irrelevant to this disclosure. The example radio audience measurement system 116 may be implemented, for example, according to any system or combination(s) of systems described in U.S. Pat. Nos. 5,481,294, 7,239,981, and/or 7,640,141, all of which are hereby incorporated by reference in their entireties.

The example print media audience measurement system 118 of FIG. 1 determines reach for one or more target groups and/or for a total population. Additionally, the example print media audience measurement system 118 determines reach for one or more subplatforms (e.g., magazines, newspapers, periodicals, books, etc.) of the print media platform. The precise methodologies and/or structures of the print media audience measurement system 118 of FIG. 1 are irrelevant to this disclosure. The example print media audience measurement system 118 may be implemented, for example, according to any system or combination(s) of systems described in U.S. Pat. Nos. 4,992,867 and 8,368,918, all of which are hereby incorporated by reference in their entireties.

While examples of various audience measurement systems are provided above, the example television audience measurement system 108, the example online audience measurement system 110, the example mobile audience measurement system 112, the example outdoor audience measurement system 114, the example radio audience measurement system 116, the example print media audience measurement system 118 and/or, more generally, the example audience measurement system 102 of FIG. 1 may be implemented using any past, present, and/or future audience measurement system(s) and/or improvement(s) thereof, and/or any combination(s) of audience measurement system(s) and/or improvement(s).

The example platform metric calculator 106 obtains (e.g., receives) effectiveness metrics from the effectiveness determiner 104. In the example of FIG. 1, obtaining the first effectiveness metric for the first media on the first platform includes measuring neurological activity of a person representative of the target group of audience members while displaying the first media to the person on the first platform. The example effectiveness determiner 104 of FIG. 1 determines the effectiveness of media platforms for presenting media to target groups. For example, the effectiveness determiner 104 may determine an effectiveness or efficiency of a platform (e.g., of media presented on a platform) on a target group as a percentage of the target group as a measure of the degree to which the group in question is engaged with and/or attentive to media when exposed to the media via the platform.

In some examples, the effectiveness determiner 104 of FIG. 1 measures neurological and/or neurophysiological responses of subjects when exposed to media (which may include, for example, programs and/or advertising of interest). In some examples, the effectiveness determiner 104 measures neurological and/or neurophysiological responses by exposing a first person representative of the target group of audience members to media and determining at least one of: engagement, attention, memory, persuasion, effectiveness, emotion, or purchase intent of the first person. The example effectiveness determiner 104 of FIG. 1 determines the effectiveness of respective platforms by measuring one or more of engagement, attention, memory, persuasion, emotion, and/or purchase intent of human subjects before, during, and/or after exposure to media of interest presented on the platforms of interest. Based on the measured effects on the people, the example effectiveness determiner 104 calculates the effectiveness of the platform. In the example of FIG. 1, the effectiveness or efficiency represents a percentage or proportion of persons who are affected (e.g., who are persuaded, whose behavior is modified, whose attention, emotional engagement, and/or memory retention are achieved, etc.) by the media or platform. An example equation to calculate effectiveness is shown below.

$$E = \frac{A_E}{A_T}$$

Equation (1)

In Equation (1), E is the effectiveness, $A_E$ is the number of people affected to a threshold degree, and $A_T$ is the total audience size. However, other measures of effectiveness or efficiency may be used. An example system to measure the effectiveness of one or more platforms is described below with reference to FIG. 2.

In some examples, the effectiveness determiner 104 of FIG. 1 determines the effectiveness of one or more platforms using surveys, questionnaires, focus groups, and/or any other manual research and/or automatic data collection method. For example, a human surveyor may present media of interest (with or without presenting other media for masking or anti-bias measures) to one or more people via a platform of interest. The human surveyor then asks questions of the people exposed to the media of interest and/or platform of interest to obtain data regarding their engagement, attention, memory, persuasion, emotion, and/or purchase intent with respect to the media of interest and/or material in the media of interest. The resulting data may be manually provided (e.g., via an input device) to the example effectiveness determiner 104 for aggregation, classification, and/or processing. In some examples, the effectiveness determiner 104 administers online surveys or surveys directly to mobile devices and/or meters. Example systems to implement the effectiveness determiner 104 using surveys is described in U.S. patent application Ser. No. 12/263,079, filed on Oct. 31, 2008, and entitled "Methods and Apparatus to Perform Consumer Surveys," the entirety of which is hereby incorporated by reference.

The example effectiveness determiner 104 of FIG. 1 outputs an effectiveness metric for each platform of interest. The effectiveness metric for a platform represents a fraction or proportion of people (overall and/or in one or more target groups) who are affected by media presented by the platform. The effectiveness determiner 104 may determine effectiveness metrics generally for a platform and/or subplatform, and/or for a platform and/or subplatform with respect to a target group and/or with respect to media of interest for presentation via the platform.

The example platform metric calculator 106 of FIG. 1 obtains (e.g., receives, accesses from storage, etc.) the reach of media platforms (e.g., from the audience measurement system(s) 102, 108-118) and obtains (e.g., receives, accesses from storage, etc.) the respective effectiveness of the media delivered via the platforms (e.g., from the effectiveness determiner 104). The example platform metric calculator 106 includes a performance estimator 120, a performance per unit cost estimator 122, and a platform selector 124.

The example performance estimator 120 of FIG. 1 estimates (e.g., calculates) the performance of media on different platforms based on the reach and the effectiveness of the platforms. The performance estimator 120 further calculates the performance of the platforms for specified target groups, which may be received from, for example, an advertiser or researcher. In the illustrated example, the performance estimator 120 calculates a media impact performance metric (I) for a given platform (P) by calculating the product of the effectiveness metric for the corresponding media with the reach of the corresponding platform in accordance with the following equation.

$$I_P = E * R_P \qquad \text{Equation (2)}$$

In Equation (2), $I_P$ is the media impact performance metric for the platform P, E is the effectiveness metric of the media, and $R_P$ is the reach of the platform P.

The example performance per unit cost estimator 122 of FIG. 1 obtains the media impact performance estimates for the various platforms under study from the performance estimator 120 and obtains costs to present media via the platforms of interest (e.g., the platforms for which performance is estimated). Based on the media impact performance metric and the respective cost, the example performance per unit cost estimator 122 estimates the platform performance of each platform (e.g., platform of interest) per unit cost (e.g., performance per dollar or other currency of interest, such as Euros, etc.). In the illustrated example, the platform performance ($PP_P$) for a given platform (P) per unit cost may be calculated in accordance with the following formula.

$$PP_P = \frac{I_P}{C_P} \qquad \text{Equation (3)}$$

In equation (3), $I_P$ is the media impact performance metric for the platform P, and C is the cost (e.g., in US dollars) to purchase 1 GRP (gross ratings point) worth of exposure on the corresponding platform P.

The example platform selector 124 of FIG. 1 selects one or more platforms and/or media (e.g., media to be delivered on a selected platform) for investment in advertising and/or programming. In the example of FIG. 1, the platform selector 124 obtains the platform performance per unit cost estimates from the performance per unit cost estimator 122, obtains a budget (e.g., an advertising campaign budget), and/or obtains a target performance. The platform selector 124 may select one or more platforms and/or subplatforms for use in advertising based on the budget, performance, and/or performance-per-unit-cost. For example, the platform selector 124 may make budget-restricted platform selection decisions to increase (e.g., maximize) the advertising impact achieved by spending the received budget. In some other examples, the platform selector 124 may make a performance-driven platform selection decision by decreasing (e.g., minimizing) a cost to obtain a threshold performance for an advertising campaign. The two example platform selection decisions (e.g., budget-restricted, performance-driven) illustrate example priorities to be used in selecting platforms and/or media for an advertising campaign.

Additionally or alternatively, the example platform selector 124 calculates a mix (e.g., an optimized mix) of media, platforms, and/or subplatforms based on the performance, the performance-per-unit-cost, and/or one or more constraints. For example, platform(s) and/or subplatform(s) may be constrained to particular audience sizes (e.g., minimum audiences per platform, minimum target group reach per platform, etc.) and/or costs (e.g., maximum campaign cost, maximum spending per platform or subplatform) to diversify an advertising campaign and avoid investing all of a campaign's budget into a single, highest-performance platform and/or subplatform. Such diversification can increase the effectiveness (e.g., success) of an advertising campaign due to the fact that different platforms and/or subplatforms can have significant non-overlapping audiences. Example constraints include lower and/or upper audience (e.g., reach) limits per platform and/or subplatform, lower and/or upper cost limits per platform and/or subplatform, and/or any other constraints or limits that may be placed on a per-platform and/or per-subplatform basis. In some examples, constraints on costs and/or audience may be placed on media to be presented via the platforms and/or subplatforms. The example platform selector 124 selects one or more media to be presented on platform(s) and/or subplatform(s) (e.g., an optimized set of media, platform(s), and/or subplatform(s) as determined by reach, cost, performance, and/or performance-per-unit-cost) based on audience and/or cost limits placed on the media, platform(s), and/or subplatform(s). Other uses are also possible.

The example audience measurement system 102, the example effectiveness determiner 104, and/or the example platform metric calculator 106 may determine reach, effectiveness, and/or platform metrics (e.g., performance, performance-per-unit-cost, etc.) for any marketing mix, advertising campaign strategy, and/or any other platform selection criteria. For example, selection criteria for distinguishing media, selecting platforms, and/or forming an advertising campaign may include time(s) of day of media presentation, target demographic groups (e.g., ages targets, gender targets, geographic targets, etc.), media genres (e.g., comedic programming or advertising, emotional advertising, children's advertising, etc.), advertising strategy (e.g., direct appeal advertising, informational advertising), and/or any other criteria. Accordingly, the example system 100 of FIG. 1 may provide advertisers with cross-platform performance metrics for multiple dimensions and/or variables. For example, the calculations represented by equations (1)-(3) above may be performed for each of a number of platforms and their values compared and/or combined to determine cross-platform metrics.

Figure 2:
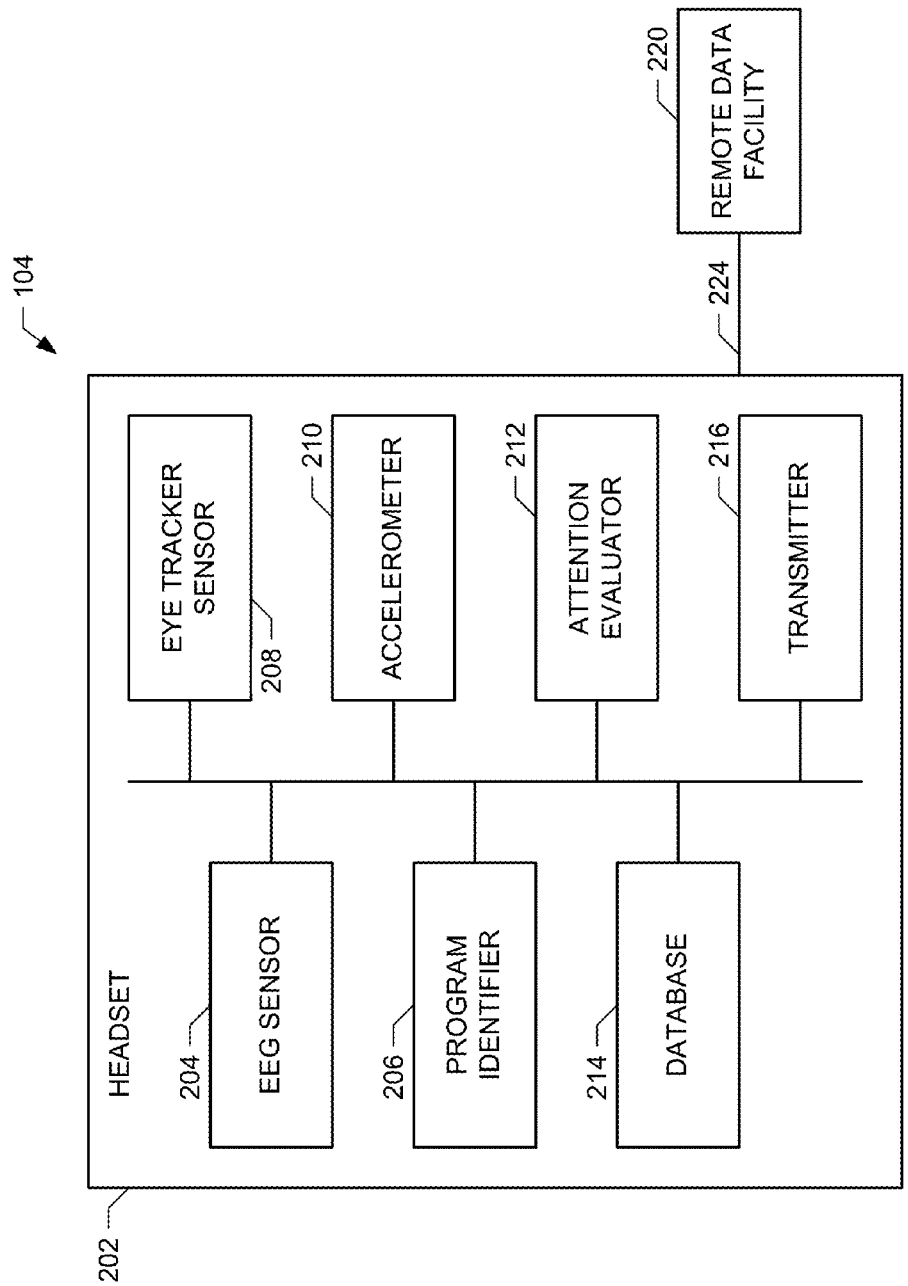
FIG. 2 is a block diagram of an example platform effectiveness measurement system to implement the effectiveness determiner of FIG. 1.

FIG. 2 is a block diagram of an example implementation of the effectiveness determiner 104 of FIG. 1. The effectiveness determiner 104 may be used for determining, processing and/or evaluating a user's attention to media to determine a measure of the effectiveness of the media. The example effectiveness determiner 104 of the illustrated example includes a headset 202, which may include, for example, one or more headset(s) disclosed in U.S. patent application Ser. Nos. 13/728,900; 13/728,913; and 13/730, 212 and U.S. Provisional Patent Application Ser. No. 61/684,640, all of which are incorporated herein by reference in their entireties. In addition, the headset 202 may be implemented for example, with the effectiveness determiner 104 of FIG. 1. The headset 202 processes electroencephalographic (EEG) signals and/or other sensor data to develop a picture of a mental state of a user including, for example, an emotional state, a state of engagement, a state of attention and/or any other neurological state. As disclosed below, the example effectiveness determiner 104 of FIG. 2 may be used to determine if the user is paying attention to a media program, to determine where a user's eyes are focused, what emotional and/or mental state the user is experiencing and/or for other applications. In the illustrated example effectiveness determiner 104, the headset 202 includes analyzer components including an EEG sensor 204 such as, for example, one or a plurality of electrode(s), a program identifier 206, an eye tracker sensor 208, an accelerometer 210, an attention evaluator 212, a database 214 and a transmitter 216. The analyzer components 204-216 are communicatively coupled via a communication link 218. The analyzer components 204-216 may be, for example, incorporated into or otherwise supported by the headset 202 such as, for example, in a compartment on a headset.

The EEG sensor 204 includes a plurality of individual electrodes to detect electrical activity along the scalp of a user. This data may be used to determine attention, memory, focus and/or other neurological states. The example eye tracker sensor 208 is used to track eye movement and/or the direction in which a user's eyes are directed. For example, the eye tracker sensor 208 may be a camera or other sensor that is incorporated into an appendage that extends from the headset 202 and is directed to one or both of the user's eyes. In other examples, the eye tracker sensor 208 may be a camera or other sensor on or near a computer, a television, a mobile phone screen or other location to gather data related to the user's eye movement. The eye tracker sensor 208 may continuously record what the user is seeing. In some examples, the eye tracker sensor 208 is placed around the middle of the user's eyebrows. Also, in some examples, the eye tracker sensor includes a monocular or binocular (e.g., one eye or two eye coverage) infra-red (IR) camera to track the pupil and/or corneal reflection positions to aide in determining a point of regard of the user's viewpoint. In some examples, the eye tracker sensor 208 incorporates and/or is used in conjunction with an accelerometer/attitude measurement system 210. Mobile eye-tracking systems that are mounted to a user's head are susceptible to erroneous measurements as the subject moves his or her head relative to the position he or she had during calibration of the system. The example accelerometer 210 continuously tracks the movement relative to the calibration position, which enables adjustment of the eye tracking data to thereby enhance the accuracy of the point-of-regard measurement from the eye-tracking sensor 208.

The eye track data may be synchronized with and/or otherwise used to corroborate the EEG data or otherwise may be used in conjunction with the EEG to determine a neurological state of the user. Eye movements provide a target of a user's attention allocation. For example, if the user is looking in the direction of a television and his or her EEG data indicates that he or she is in a state of engagement or attention, the eye track data and EEG data together demonstrate that the attention was likely directed to the television.

The example system of FIG. 2 also includes database 214 for local storage of raw data, processed data, result data, history logs, programming data from a media source, and/or any other type of data. The transmitter 216 of the illustrated example communicates the data at any stage of processing and/or the results of the analysis from the headset 202 to a remote data facility 220, as disclosed in more detail below.

In some example implementations, the effectiveness determiner 104 is provided with a program identifier 206 to collect audience measurement data. The example effectiveness determiner 104 determines if a user's neurological state indicates that the user is focused (e.g., engaged with the media) while watching a certain media. The program identifier 206 identifies media to which the user is exposed. The program identification can be done with any technology, for example, the program can be identified by collecting audio codes and/or signatures using a microphone on the headset 202 to collect audio signals as disclosed in Thomas, U.S. Pat. No. 5,481,294, which is incorporated by reference herein in its entirety. The program identifier 206 collects data concerning the media, such as, for example, a television show, an advertisement, a movie, a news clip, radio program, a web page, or any other media and identifies the media (e.g., content or advertisement) based on the collected data and/or forwards the collected data to another device to perform the identification.

In the collection of audience measurement data, the example effectiveness determiner 104 gathers EEG data from the EEG sensors 204 of the headset 202. The effectiveness determiner 104 gathers eye tracking data from the eye tracking sensor 208 to determine which direction the user is gazing during the media broadcast. The attention evaluator 212 uses data from the EEG sensor 204 and the eye tracker sensor 208 to determine if a user is paying attention to the media. For example, if the EEG sensors 204 detect brain waves (e.g., electrical activity) indicative of increased thought, and the eye tracking sensor 208 determines that the user is looking at the TV, the attention evaluator 212 will output a signal (e.g., an effectiveness metric) that the user is focused and immersed in that particular media program being broadcast. However, if the program identifier 206 determines a certain program is being presented, and the EEG sensors 204 indicate decreasing brain activity, or if the eye tracker sensor 208 determines the user is not looking at the TV, then the attention evaluator 212 will output a signal (e.g., an effectiveness metric) that the user is not focused or immersed on that particular media program.

To determine user emotional and/or mental state based on the EEG data, the attention evaluator 212 analyzes the EEG data to evaluate brain activity in particular frequency bands of the EEG data and/or in particular regions of the brain. For example, EEG data can be classified in various bands. Brainwave frequencies include delta, theta, alpha, beta and gamma frequency ranges. Delta waves are classified as those less than about 4 Hertz (Hz) and are prominent during sleep. Theta waves have frequencies between about 3.5 Hz to about 7.5 Hz and are associated with memories, attention, emotions, and sensations. Theta waves are typically prominent during states of internal focus. Alpha frequencies reside between about 7.5 Hz and about 13 Hz and typically peak around 10 Hz. Alpha waves are prominent during states of relaxation. Beta waves have a frequency range between about 14 Hz and about 30 Hz. Beta waves are prominent during states of motor control, long range synchronization between areas, analytical problem solving, judgment, and decision making. Gamma waves occur between about 30 Hz and about 100 Hz and are involved in binding of different populations of neurons together into a network for the purpose of carrying out a certain cognitive or motor function, as well as in attention and memory. Because the skull and dermal layers attenuate waves in this frequency range, brain waves above about 75 Hz (e.g., high gamma band or kappa band) are less easily measured than waves in lower frequency bands. Assessments and/or calculations of the relationship(s) and correlation(s) of the frequency bands and regions of activity of the EEG data are used to determine an emotional or mental state of a person including, for example, attention, emotional engagement, memory or resonance, etc.

For example, the regions of brain activity, the interaction between regions of brain activity, and/or the interactions including couplings between frequency bands signify particular mental states. Also, inter-regional coherencies of frequency bands as measured from gain and/or phase may be used to estimate the effectiveness of media in evoking a desired response (e.g., attention) in a subject. In addition, inter-hemispheric measurement, asymmetry in one or more frequency bands, asymmetry in inter-regional intra-hemispheric coherence and/or asymmetry in inter-regional intra-hemispheric inter-frequency coupling may be used to measure of emotional engagement.

For example, the attention evaluator 212 may be used to determine or calculate an interaction between a first frequency band of the EEG data and a second frequency band of the EEG by detecting a first pattern of oscillation in the first frequency band, detecting a second pattern of oscillation in the second frequency band and identifying a degree of phase synchrony between the first pattern and the second pattern. The media effectiveness evaluation, in this example, is based on the degree of phase synchrony.

In other example, the attention evaluator 212 detects a first pattern of oscillation in a first frequency band of EEG data and detects a second pattern of oscillation in a second frequency band of the EEG data. The attention evaluator 212 identifies a degree of phase synchrony between the first pattern from the first frequency band and the second pattern from the second frequency band by detecting a repeating sequence of relative phase angles between the first pattern of oscillation in the first frequency band and the second pattern of oscillation in the second frequency band. The media effectiveness evaluation, in this example, is based on the degree of the phase synchrony at a specific point in time.

In other example, the attention evaluator 212 analyzes EEG data to determine effectiveness data for media based on a degree of asymmetry between a first frequency band of the EEG data for measured in a first hemisphere of a brain of a panelist and a second frequency band of the EEG data measured in a second hemisphere of the brain. The degree of asymmetry is identified by detecting a first amplitude of the first frequency band and detecting a second amplitude of the second frequency band. The attention evaluator 212 compares the first amplitude and the second amplitude to determine a difference between the first amplitude of the first frequency band and the second amplitude of the second frequency band. Also, the attention evaluator 212 assigns the degree of asymmetry to the relationship between the first frequency band and the second frequency band based on the difference between the first amplitude of the first frequency band and the second amplitude of the second frequency band. Thus, in this example, the effectiveness of the media is based on a degree of inter-frequency, inter-hemispheric asymmetry, which is identified by comparing the amplitudes of two frequency bands from different hemispheres.

In another example, the attention evaluator 212 analyzes an interaction between a first frequency band of EEG data and a second frequency band of EEG by calculating a degree of phase synchrony or amplitude synchrony. The phase synchrony or amplitude synchrony is determined by detecting a first pattern of oscillation in the first frequency band and detecting a second pattern of oscillation in the second frequency band. In addition, the attention evaluator 212 detects a repeating sequence of phase angles or relative amplitude between the first pattern of oscillation in the first frequency band and the second pattern of oscillation in the second frequency band. The effectiveness of the media (e.g., a determined effectiveness metric) is based on the interaction.

In still another example, the attention evaluator 212 assesses the effectiveness of media based on a first asymmetry between two amplitudes from two frequency bands and a second asymmetry between two different amplitudes of the frequency bands. Specifically, in this example, the attention evaluator 212 identifies a first asymmetry in two frequency bands of EEG data related to a first portion of the media. The first asymmetry identified by comparing a first amplitude of the first frequency band and a second amplitude of the second frequency band to determine a first difference between the first amplitude of the first frequency band and the second amplitude of the second frequency band. In addition, a first value is assigned to the first asymmetry based on the first difference between the first amplitude of the first frequency band and the second amplitude of the second frequency band. The attention evaluator 212 also identifies a second asymmetry in two frequency bands of EEG data related to a second portion of the media. The first and second portions of the media may be temporally disparate portions of the media or different portions that are concurrently experienced by the panelist (e.g., video and audio). The second asymmetry is identified by comparing a third amplitude of the first frequency band and a fourth amplitude of the second frequency band to determine a second difference between the third amplitude of the first frequency band and the fourth amplitude of the second frequency band. A second value is assigned to the second asymmetry based on the second difference between the third amplitude of the first frequency band and the fourth amplitude of the second frequency band. The attention evaluator 212 assess an effectiveness of the media for each of the first and second portions based on the first value of the first asymmetry and the second value of the second asymmetry.

Data reflected of the user paying attention, the user not paying attention, the user in a state of semi-involvement with the program, or other user mental state, and the identity of the program are storable in the database 214 and transmittable by the transmitter 216 to an output including, for example, the remote data facility 220. Raw data, processed data, a history log or an indicator of audience measurement also may be transmitted to the remote data facility 220 for collection. The remote data facility 220 may be, for example, a marketing company, a broadcast company, an entertainment studio, a television network and/or any other organization that might benefit from or otherwise desire to know when users are and/or are not focused on broadcast programs and what those programs are. In some examples, the headset 202 is communicatively coupled to the remote data facility 220 via a communication channel 224 such as common telephone line, a landline, an internet connection, radio waves, and/or any other communication technology capable of sending signals. This example allows broadcasting companies and/or marketing personnel to analyze which programs people are watching, when they are watching the programs and/or when they are focused during the broadcast.

Though the examples disclosed above are described in relation to the example headset 202, one or more of the analysis components may be located off of a headset. For example, the attention evaluator 212 may analysis EEG gathered from a headset, but the attention evaluator 212 is incorporated into a separate device such as, for example, a desktop computer, a laptop computer, a tablet, etc.

While an example implementation of the effectiveness determiner 104 of FIG. 1 is described in FIG. 2, other systems may be used to implement all or part of the effectiveness determiner 104. Examples of systems that may be used are disclosed in U.S. Pat. Nos. 6,099,319 and 8,230,457, all of which are hereby incorporated by reference in their entireties, among others.

Figure 3:
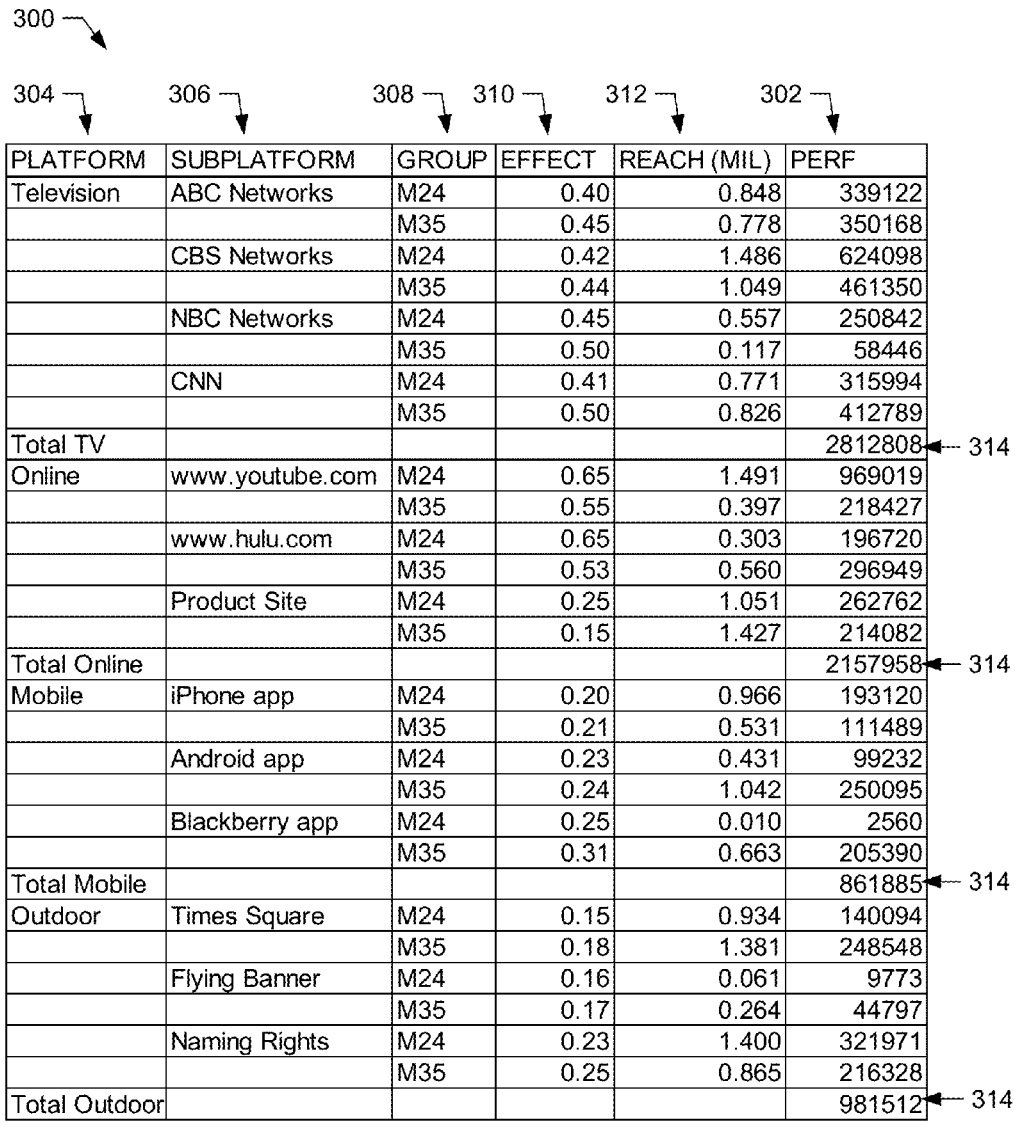
FIG. 3 is a table illustrating example calculations of effectiveness of a media campaign for multiple platforms.

FIG. 3 is a table 300 illustrating example calculations of effectiveness of a media campaign for multiple platforms. The example table 300 of FIG. 3 may be generated and/or populated by the example audience measurement systems 102, 108-118, the example effectiveness determiner 104, and/or the example performance estimator 120 of FIG. 1. The example table 300 of FIG. 3 may be stored in a computer readable storage medium such as a memory (e.g., the memories 914, 916 of FIG. 9) or a mass storage device (e.g., the mass storage device 928 of FIG. 9). Other examples of storage devices that may be used to store the table 300 are described below with reference to FIG. 9.

The example table 300 provides values for the performance metric 302 (e.g., the media impact performance metric $I_P$ of equations (2) and/or (3)) for combination(s) of designated platforms 304, subplatforms 306, and/or target groups 308. The example subplatforms 306 represent platform-specific (e.g., exclusive to one or more, but not all, platforms) or platform agnostic subsets of a platform (e.g., television and/or radio channels and/or networks, web sites, mobile device brands, etc.). Furthermore, the example platforms 304 and/or subplatforms 306 may be further divided into times, time slots, days of the week, dates, and/or any other temporal division. The time slots for different platforms 304 and/or subplatforms 306 in the table 300 of FIG. 3 may be similar, identical, overlapping, or different. The example target groups 308 represent persons of interest for whom the effectiveness, reach, and/or performance may be determined. In the example of FIG. 3, the target groups 308 are not platform-specific but, instead, represent persons of interest to whom an advertiser would most prefer to direct advertising efforts via any available platform.

The example table 300 of FIG. 3 includes an effectiveness or efficiency metric 310 (e.g., effectiveness E in equations (1) and/or (2) above) and reach 312 (e.g., reach $R_P$ in Equation (2) above) of each combination of platform 304, subplatform 306, and target group 308. The example reach 312 data in the table 300 of FIG. 3 is expressed in millions of people (e.g., a reach of "1" in Table 3 is equal to a reach of one million people). However, reach 312 may be expressed using any other scale. The efficiency metrics 310 represent respective proportions or percentages of persons in the target group 308 who are substantially affected (e.g., who are persuaded, whose behavior is modified, whose attention, emotional engagement, and/or memory retention are achieved, etc.) by the corresponding platform 304 and subplatform 306. The example effectiveness determiner 104 may determine the effectiveness or efficiency metric 310 using the example equation (1).

The example table 300 of FIG. 3 includes an effectiveness or efficiency metric 310, reach 312, and a platform metric 314 (e.g., platform performance) of each of the combinations of platform 304, subplatform 306, and target group 308. The example efficiency metric 310 of FIG. 3 may be populated by the effectiveness determiner 104 of FIG. 1. The reach 312 for the example television, online, mobile, and outdoor platforms 304 and associated subplatforms 306 and target groups 308 may be populated by the example television audience measurement system 108, the example online audience measurement system 110, the example mobile audience measurement system 112, and the example outdoor audience measurement system 114, respectively.

The example performance estimator 120 calculates the performance metric 302 (e.g., the media impact performance metric $I_P$) for each of the combinations of platform 304, subplatform 306, and target group 308 from the corresponding effectiveness 310 and reach metrics 312. For example, the performance estimator 120 of FIG. 1 calculates the product of the effectiveness 310 and the reach values 312 as the performance metric 302 for the corresponding target group 308 on a subplatform 306 of a platform 304. The example performance estimator 120 may calculate the performance metrics 302 using the example equation (2).

The example performance estimator 120 further determines the platform metrics 314 (e.g., a total platform performance) for each of the example platforms 304 by summing the performance metrics 302 of each of the example subplatforms 306 and target groups 308 using the example equation (4) below.

$$TP_P = \sum_{S=1}^{n} I_S \qquad \text{Equation (4)}$$

In the example equation (4), $I_S$ is the performance metric 302 (e.g., the media impact performance metric) for a subplatform 306 and/or target group 308, $TP_P$ is the platform metric 314 (e.g., the total platform performance) for the subplatform(s) 306 and/or group(s) 308 of the selected platform P, and n is the number of subplatforms for the selected platform 304.

The example platform metric 314 represents a total performance (e.g., considering reach 312 and effectiveness 310 on each selected subplatform 306 and target group 308) for each of the example platforms 304. The example platform metrics 314 may be used to select between the platforms 304 for an advertising campaign. In some examples, the platform metrics 314 may be adjusted based on overlap statistics for the subplatforms 306 and/or target groups 308.

FIG. 4 is a table 400 illustrating example calculations of cost effectiveness of a media campaign for multiple platforms. The example table 400 of FIG. 4 may be generated by the example performance estimator 120 and/or the example performance-per-unit-cost estimator 122 of FIG. 1 based on the data from the table 300 of FIG. 3. For example, the table 400 of FIG. 4 includes the platform 304, subplatform 306, and group 308 breakdowns from the table 300 of FIG. 3, as well as the corresponding performance metrics 302.

The example table 400 further includes corresponding costs 402 (e.g., cost(s) $C_P$ of the example equation (3)) for the example platforms 304 and subplatforms 306. As illustrated in FIG. 4, the cost 402 may be equal across certain target groups 308 due to the nature of a platform 304 and/or a subplatform 306. For example, advertising on a particular network will cost the same regardless of the target age and gender group. However, costs may be different between certain target groups 308 (e.g., time slots and/or geographic regions in the television platform). Additionally, costs may be different for the same subplatform 306 when multiple dimensions of subplatform are used.

Using the performance 302 (e.g., $I_P$ of the example equation (3)) and the cost 402 (e.g., cost(s) $C_P$ of the example equation (3)), the example performance-per-unit-cost estimator 122 of FIG. 1 determines a performance per unit cost 404 (e.g., performance per U.S. dollar, $PP_P$ of the example equation (3)) for each of the combinations of platform 304, subplatform 306, and target group 308. For example, the performance-per-unit-cost estimator 122 may use the example equation (3) to calculate the performance per unit cost 404 of FIG. 4. In the example table 400, a higher performance per unit cost 404 represents a better advertisement platform 304 and/or subplatform 306, because more people in the target group 308 are affected by the advertisement per dollar spent on the advertisement.

The example table 400 of FIG. 4 further includes platform metrics 406 (e.g., platform performance, platform costs, and platform performance per unit cost). The example platform selector 124 of FIG. 1 may use the performance per unit cost 404 and/or the platform metrics 406 of FIG. 4 to select one or more combinations of platforms 304 and/or subplatforms 306 for an advertisement. In some examples, the platform selector 124 aggregates (e.g., sums, weights and sums, etc.) the performance per unit cost 404 by platform 304, subplatform 306, and/or by target group 308 to obtain an aggregate performance per unit cost.

In some examples, the platform selector 124 selects multiple platforms and/or subplatforms to reach different individuals in a universe. Because two different individuals may access different platforms and/or subplatforms (e.g., a first individual watches a first television channel at the same time a second individual watches a second television channel or surfs the Internet, a first individual is exposed to media via a platform that a second individual is never exposed to, etc.), the example platform selector 124 of FIG. 1 may select multiple platforms to increase an overall effectiveness of an advertising campaign rather than simply investing the entirety of an advertising budget into the platform and/or subplatform having the highest performance-per-unit-cost.

The example platform selector 124 of FIG. 1 may further determine a campaign effectiveness 408. The example campaign effectiveness 408 of FIG. 4 includes the total campaign performance 410, a total campaign cost 412, and a total performance per unit cost 414. The example campaign effectiveness metrics 408 are based on the selection of the platforms 304 illustrated in the example table 400 of FIG. 4. The example campaign performance 410 of FIG. 4 is a sum of the performance metrics 302 of the selected platforms 304. The example performance estimator 120 of FIG. 1 may determine the campaign performance using the following equation (5).

$$P_{campaign} = \sum_{P=1}^{m} TP_P \quad \text{Equation (5)}$$

In equation (5), $P_{campaign}$ is the estimated performance of the campaign (e.g., the total campaign performance 410), $TP_P$ is the total performance for platform P, and m is the number of platforms 304 in the campaign.

The example campaign cost 412 is a sum of the cost 402 of the platforms 304, divided by a factor of 2 to reflect that the example costs 402 are duplicated in the table 400. The example campaign performance per unit cost 414 is determined from the campaign performance 410 and the campaign costs 412. The example performance per unit cost 414 may determine the campaign performance per unit cost 414 using an equation similar to equation (3) described above, substituting the estimated performance of the campaign $P_{campaign}$ (e.g., the campaign performance 410) for the platform performance $PP_P$ and substituting the campaign costs 412 for the platform cost $C_P$.

Furthermore, one or more platforms 304 and/or subplatforms 306 may have overlapping individuals (e.g., individuals who may be counted on both platforms, which can artificially inflate a total reach if not corrected for). In some examples, the platform selector 124 calculates or estimates a number of overlapping individuals between platform(s) 304, subplatform(s) 306, and/or group(s) 308 based on overlap information. The example platform selector 124 adjusts the performance metric 302 and/or the performance-per-unit-cost 404 based on the overlap information. The example platform selector 124 selects multiple platforms 304, subplatforms 306, and/or groups 308 based on the performance metrics 302, the performance-per-unit-cost metric 404, the platform metrics 406, the campaign metrics 408, and/or the overlap information to further improve an advertising campaign.

While example platforms, subplatforms, and target groups are illustrated in FIGS. 3 and 4, additional and/or alternative dimensions of platform, subplatform, and/or target group may be used. For example, the subplatforms 306 of the television platform 304 may be further divided into particular programs, time slots, and/or geographic regions, among other things. Additionally or alternatively, the example target groups 308 may be further divided into geographic regions, income groups, and/or national origin, among other things.

The example data in the tables 300, 400 of FIGS. 3 and/or 4 are provided for illustrative purposes only, and do not reflect actual measured data. Accordingly, the respective performances, costs, and/or performances-per-unit-cost are examples and may change over time and/or based on measurement methodology.

While an example manner of implementing the system 100 of FIG. 1 is illustrated in FIGS. 1 and/or 2, one or more of the elements, processes and/or devices illustrated in FIGS. 1 and/or 2 may be combined, divided, re-arranged, omitted, eliminated and/or implemented in any other way. Further, the example audience measurement system 102, the example effectiveness determiner 104, the example platform metric calculator 106, the example television audience measurement system 108, the example online audience measurement system 110, the example mobile audience measurement system 112, the example outdoor audience measurement system 114, the example radio audience measurement system 116, the example print media audience measurement system 118, the example performance estimator 120, the example performance per unit cost estimator 122, the example platform selector 124, the example program identifier 206, the example attention evaluator 212, the example database 214, the example transmitter 216, the example remote data facility 220 and/or, more generally, the example system 100 of FIGS. 1 and/or 2 may be implemented by hardware, software, firmware and/or any combination of hardware, software and/or firmware. Thus, for example, any of the example audience measurement system 102, the example effectiveness determiner 104, the example platform metric calculator 106, the example television audience measurement system 108, the example online audience measurement system 110, the example mobile audience measurement system 112, the example outdoor audience measurement system 114, the example radio audience measurement system 116, the example print media audience measurement system 118, the example performance estimator 120, the example performance per unit cost estimator 122, the example platform selector 124, the example program identifier 206, the example attention evaluator 212, the example database 214, the example transmitter 216, the example remote data facility 220 and/or, more generally, the example system 100 could be implemented by one or more analog or digital circuit(s), logic circuits, programmable processor(s), application specific integrated circuit(s) (ASIC (s)), programmable logic device(s) (PLD(s)) and/or field programmable logic device(s) (FPLD(s)). When reading any of the apparatus or system claims of this patent to cover a purely software and/or firmware implementation, at least one of the example audience measurement system 102, the example effectiveness determiner 104, the example platform metric calculator 106, the example television audience measurement system 108, the example online audience measurement system 110, the example mobile audience measurement system 112, the example outdoor audience measurement system 114, the example radio audience measurement system 116, the example print media audience measurement system 118, the example performance estimator 120, the example performance per unit cost estimator 122, the example platform selector 124, the example program identifier 206, the example attention evaluator 212, the example database 214, the example transmitter 216, the example remote data facility 220 is/are hereby expressly defined to include a tangible computer readable storage device or storage disk such as a memory, a digital versatile disk (DVD), a compact disk (CD), a Blu-ray disk, etc. storing the software and/or firmware. Further still, the example system 100 of FIGS. 1 and/or 2 may include one or more elements, processes and/or devices in addition to, or instead of, those illustrated in FIGS. 1 and/or 2, and/or may include more than one of any or all of the illustrated elements, processes and devices.

Figure 5:
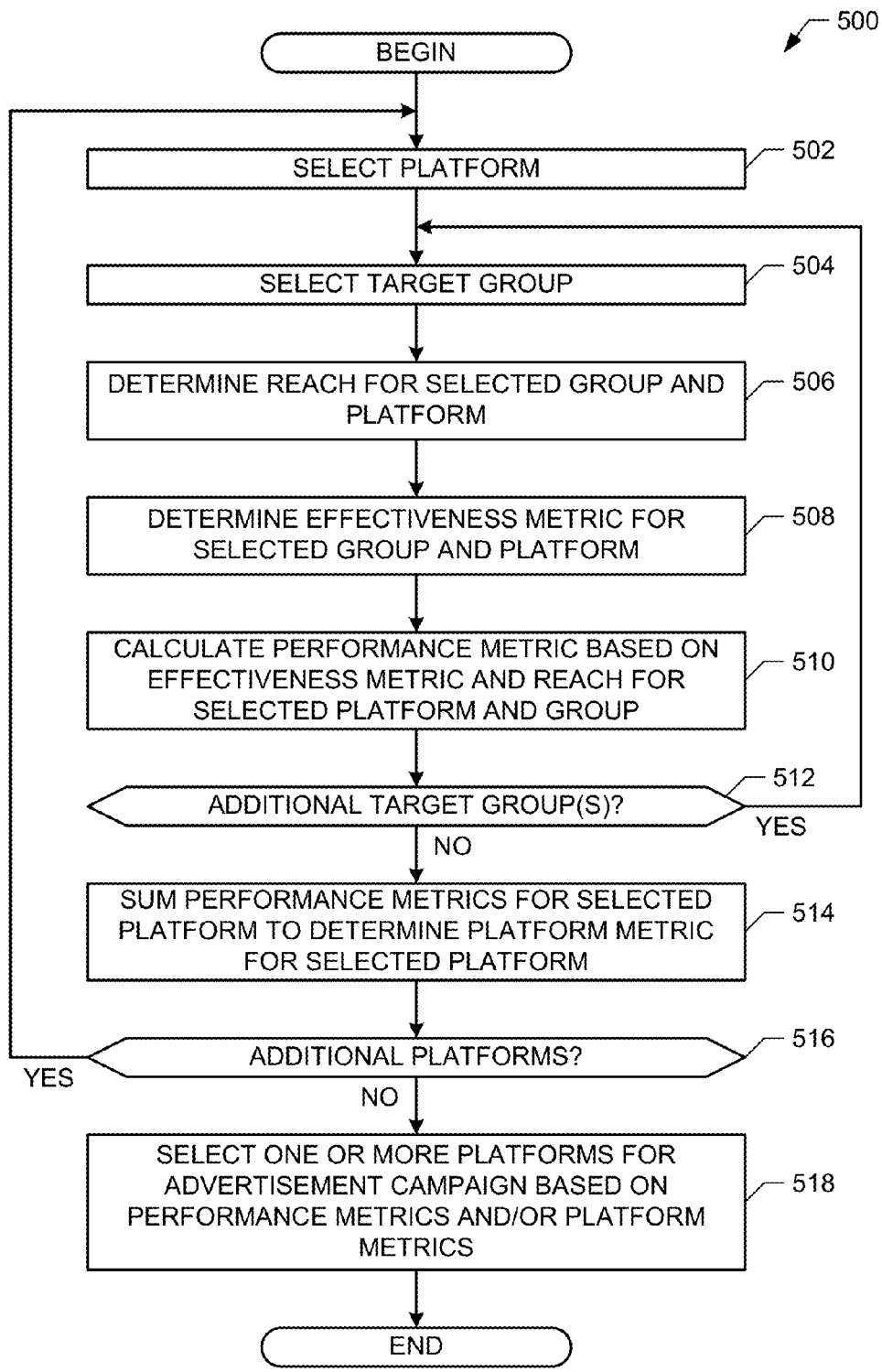
FIG. 5 is a flowchart representative of example computer readable instructions which, when executed, cause a computer to implement the example system of FIG. 1 to determine platform metrics.
Figure 6:
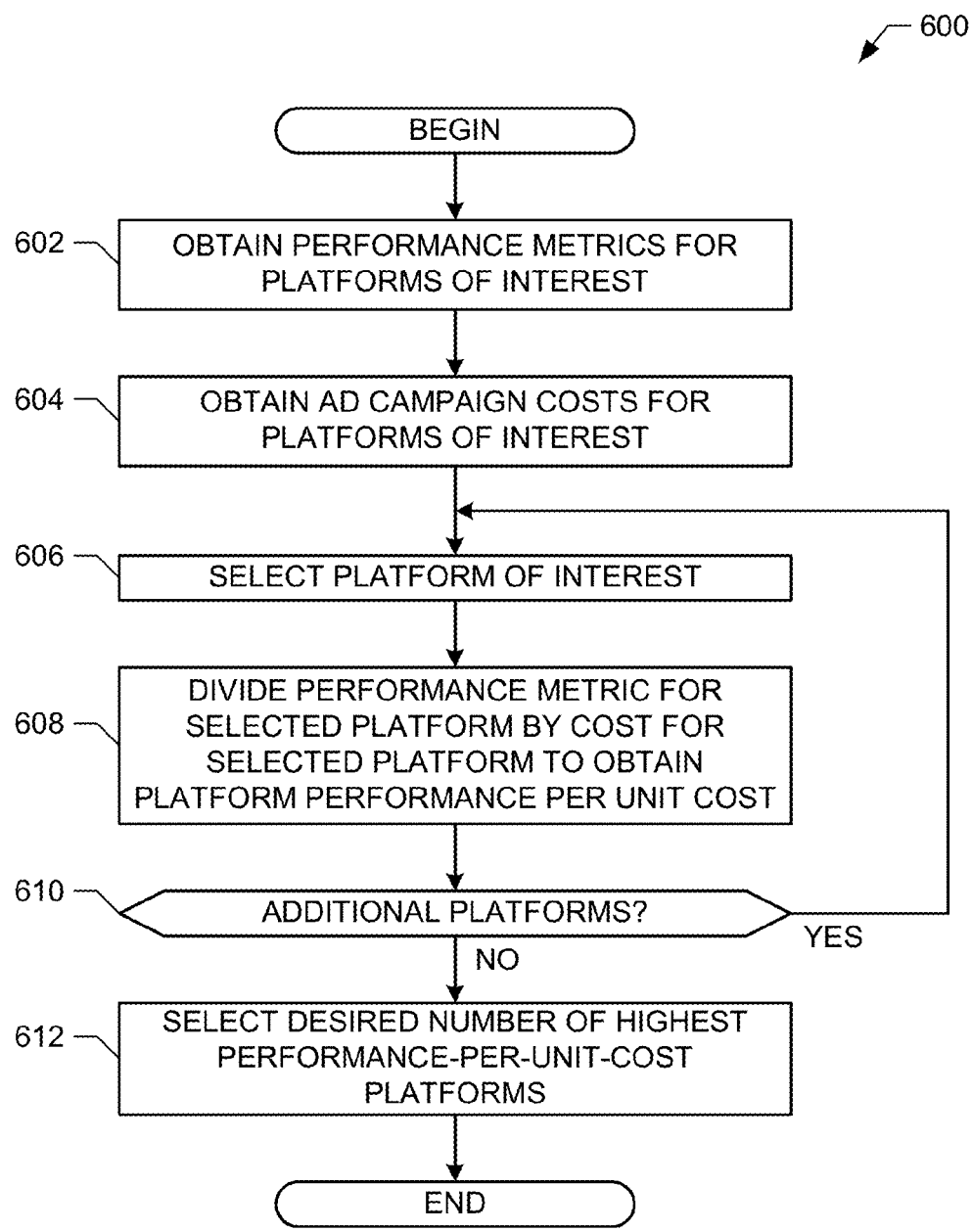
FIG. 6 is a flowchart representative of example computer readable instructions which, when executed, cause a computer to implement the example system of FIG. 1 to determine platform performance per unit cost for a media campaign.
Figure 7:
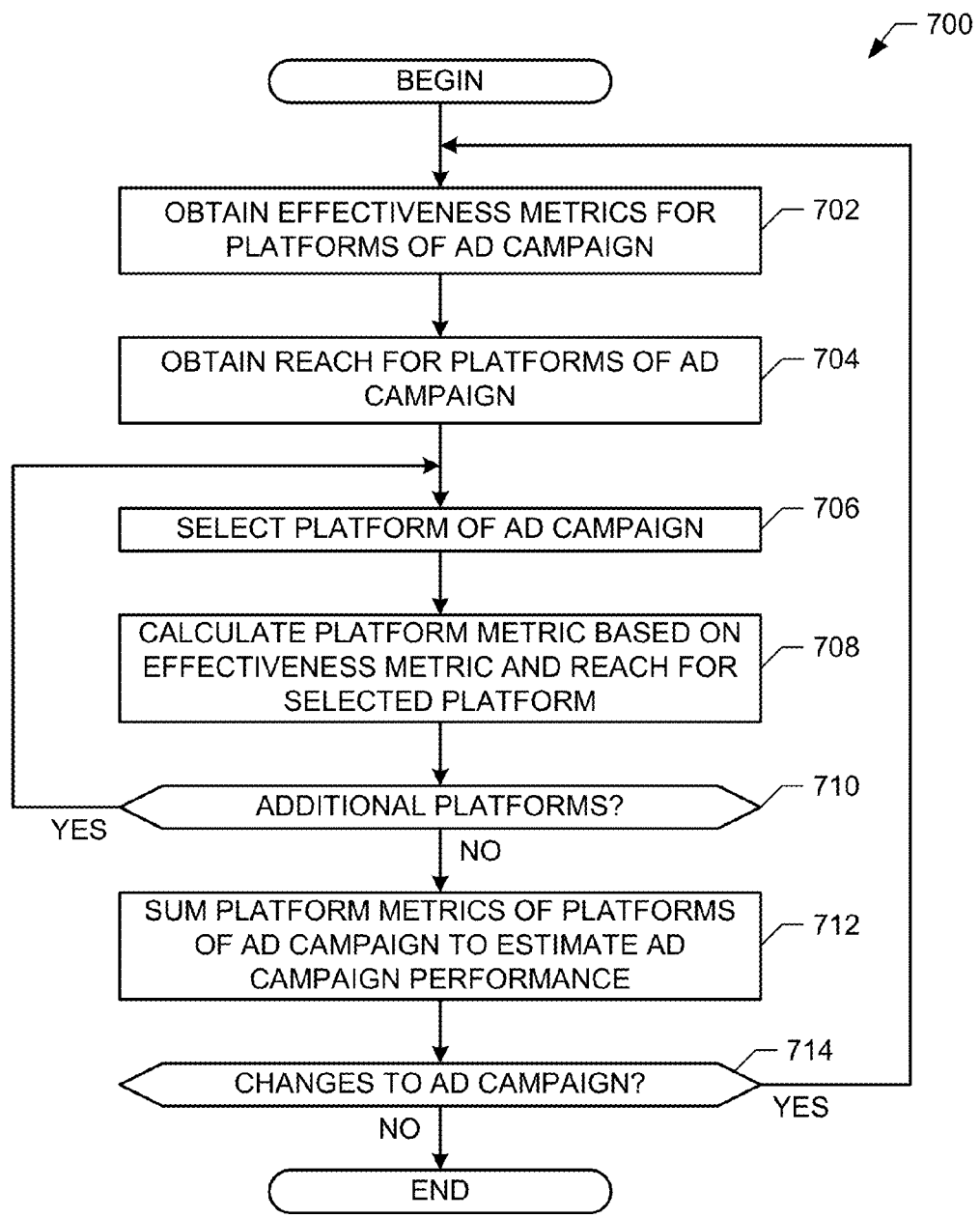
FIG. 7 is a flowchart representative of example computer readable instructions which, when executed, cause a computer to implement the example system of FIG. 1 to estimate performance of a media campaign.

Flowcharts representative of example machine readable instructions for implementing the system 100 of FIGS. 1 and/or 2 are shown in FIGS. 5, 6, and 7. In this example, the machine readable instructions comprise programs for execution by a processor such as the processor 912 shown in the example processor platform 900 discussed below in connection with FIG. 9. The programs may be embodied in software stored on a tangible computer readable storage medium such as a CD-ROM, a floppy disk, a hard drive, a digital versatile disk (DVD), a Blu-ray disk, or a memory associated with the processor 912, but the entire programs and/or parts thereof could alternatively be executed by a device other than the processor 912 and/or embodied in firmware or dedicated hardware. Further, although the example programs are described with reference to the flowcharts illustrated in FIGS. 5-8, many other methods of implementing the example system 100 may alternatively be used. For example, the order of execution of the blocks may be changed, and/or some of the blocks described may be changed, eliminated, or combined.

As mentioned above, the example processes of FIGS. 5-8 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals. As used herein, "tangible computer readable storage medium" and "tangible machine readable storage medium" are used interchangeably. Additionally or alternatively, the example processes of FIGS. 5-8 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable device or disk and to exclude propagating signals. As used herein, when the phrase "at least" is used as the transition term in a preamble of a claim, it is open-ended in the same manner as the term "comprising" is open ended.

FIG. 5 is a flowchart representative of example computer readable instructions 500 which, when executed, cause a computer to implement the example system 100 of FIG. 1 to determine platform (and/or subplatform) metrics. The example instructions 500 of FIG. 5 may be executed to implement the example audience measurement systems 102, 108-118, the example effectiveness determiner 104, the example platform metric calculator 106, the example performance estimator 120, and/or the example platform selector 124 of FIG. 1.

The example platform metric calculator 106 of FIG. 1 selects a first media platform (e.g., the platform 304 of FIG. 3) (and/or subplatform (e.g., the subplatform 306 of FIG. 3)) (block 502). For example, the platform metric calculator 106 may select the first media platform 304 (and/or subplatform 306) from a set of platforms 304 (and/or subplatforms 306) of interest. In some examples, selection of platforms 304 and/or the platforms of interest that may be selected are determined based on a proposed advertising campaign. In some examples, the platform metric calculator 106 may select from all available platforms 304 and/or subplatforms 306, or from platforms 304 and/or subplatforms 306 for which reach and/or effectiveness data can be obtained. The example platform metric calculator 106 selects a target group (e.g., the group 308 of FIG. 3) (block 504). The target group 308 may be a distinct subset of an audience of the selected media platform 304 (and/or subplatform 306).

The example audience measurement systems 102, 108-118 determine reach (e.g., the reach 312 of FIG. 3, reach $R_P$ in equation (2)) for the selected group 308 and selected platform 304 (and/or subplatform 306) (block 506). For example, the performance estimator 120 may request reach 312 for the selected group 308 and selected platform 304 (and/or subplatform 306) from a corresponding one of the example television audience measurement system 108, the example online audience measurement system 110, the example mobile audience measurement system 112, the example outdoor audience measurement system 114, the example radio audience measurement system 116, and/or the example print media audience measurement system 118. In some examples, block 506 may be replaced and/or modified to determine additional and/or alternative platform 304 (and/or subplatform 306) metrics (e.g., ratings). The example effectiveness determiner 104 of FIG. 1 determines an effectiveness or efficiency (e.g., the effectiveness metric 310 of FIG. 3, the effectiveness metric E of equations (1) and (2)) for the selected group 308 and selected platform 304 (and/or subplatform 306) (block 508). For example, the effectiveness determiner 104 may measure and/or reference measurements of neurophysiological reactions of people within or similar to the selected target group 308 to media delivered via the selected platform 304 (and/or subplatform 306).

The example performance estimator 120 of FIG. 1 calculates a performance metric (e.g., the performance metric 302 of FIG. 3, the media impact performance metric $I_P$ of equations (2) and (3)) based on the effectiveness metric 310 and the reach 312 for the selected group 308 and selected platform 304 (and/or subplatform 306) (block 510). For example, the performance estimator 120 may determine a product of the effectiveness metric 310 and the reach 312 to calculate the performance metric 302. The example performance estimator 120 determines if there are additional target groups 308 (block 512). If there are additional groups 308 (block 512), control returns to block 504 to select the next target group 308 for the same platform 304 (and/or subplatform 306).

When there are no additional target groups 308 (block 512), the example performance estimator 120 sums the performance metrics 302 for the selected platform 304 (and/or subplatform 306) to determine a platform 304 (and/or subplatform 306) metric (e.g., the total platform performance $TP_P$ of equation (4)) for the selected platform 304 (block 514). For example, the performance estimator 120 may determine a total performance for the selected platform 304 (and/or subplatform 306) to enable a comparison of the performance of the selected platform 304 (and/or subplatform 306) as a whole with other platforms 304 (and/or subplatforms 306).

The example performance estimator 120 determines whether there are additional platforms 304 (and/or subplatforms 306) to analyze (block 516). If there are additional platforms 304 (and/or subplatforms 306) (e.g., for comparison with other platforms 304 and/or subplatforms 306) to analyze (block 516), control returns to block 502 to select the next platform 304 (and/or subplatform 306). When there are no more platforms 304 (and/or subplatforms 306) to analyze (block 516), the example platform selector 124 selects one or more platforms 304 (and/or subplatforms 306) for an advertisement campaign based on the performance metrics 302 and/or the platform 304 (and/or subplatform 306) metrics (block 518). For example, the platform selector 124 may select one or more platforms 304 (and/or subplatforms 306) by comparing the performance metrics 302 and/or the platform (and/or subplatform) metrics to determine better platforms 304 (and/or subplatforms 306) for advertising. In some examples, the platform selector 124 selects multiple platforms 304 and/or subplatforms 306 to compensate for overlapping audiences. In some examples, the example platform selector 124 calculates a mix (e.g., an optimized mix) of media, platforms 304, and/or subplatforms 306 based on the performance 302, the costs 402, the performance-per-unit-cost 404, and/or one or more constraints. Example constraints include lower and/or upper audience (e.g., reach) limits per platform and/or subplatform, lower and/or upper cost limits per platform and/or subplatform. The example platform selector 124 may select between the platforms 304, subplatforms 306, and/or media to increase (e.g., maximize) a performance of the campaign and/or decrease (e.g., minimize) a cost of an advertising campaign within the constraints set on each of the platforms 304, subplatforms 306, and/or media under consideration. In some examples, the platform selector 124 outputs a list of selected platforms 304 (and/or subplatforms 306) as a recommendation for informing an advertising campaign. The example instructions 500 may then end.

FIG. 6 is a flowchart representative of example computer readable instructions 600 which, when executed, cause a computer to implement the example system 100 of FIG. 1 to determine platform (e.g., the platforms 304 of FIG. 4) (and/or subplatform (e.g., the subplatforms 306 of FIG. 4)) performance per unit cost (e.g., the performance per unit cost 404 of FIG. 4) for a media campaign. The example instructions 600 of FIG. 6 may be executed to implement the example platform metric calculator 106, the example performance estimator 120, the example performance per unit cost estimator 122, and/or the example platform selector 124 of FIG. 1.

The example performance per unit cost estimator 122 of FIG. 1 obtains (e.g., receives, accesses from storage) platform 304 (and/or subplatform 306) metrics (e.g., the media impact performance metric $I_P$ of equation (3), the total platform performance $TP_P$ of equation (4)) for platforms 304 (and/or subplatforms 306) of interest (block 602). For example, the performance per unit cost estimator 122 may obtain performance metrics 302 from the performance estimator 120 of FIG. 1 (e.g., based on effectiveness metrics 310 and reach 312 of the platform 304 and/or subplatform 306 of FIG. 3). The example performance per unit cost estimator 122 obtains (e.g., receives, accesses from storage) ad campaign costs (e.g., costs 404 of FIG. 4) for the platforms 304 (and/or subplatforms 306) of interest (block 604). Costs 404 may be obtained via manual data entry and/or stored on a storage device for retrieval by the example performance per unit cost estimator 122.

The example performance per unit cost estimator 122 selects a media platform 304 (and/or subplatform 306) of interest (block 606). For example, the performance per unit cost estimator 122 may select a first media platform 304 (and/or subplatform 306) from a set of platforms 304 (and/or subplatforms 306) of interest. The example performance per unit cost estimator 122 divides the performance metric 302 for the selected platform 304 (and/or subplatform 306) by a cost (e.g., a cost of advertising) for the selected platform 304 (and/or subplatform 306) to obtain a platform 304 (and/or subplatform 306) performance per unit cost 404 (e.g., the platform performance per unit cost ($PP_P$)) (block 608). The example performance per unit cost 404 may be expressed in units of performance per dollar or any other currency or unit of cost.

The example performance per unit cost estimator 122 determines whether there are additional platforms 304 (and/or subplatforms 306) of interest to be analyzed (block 610). If there are additional platforms 304 (and/or subplatforms 306) to be analyzed (block 610), control returns to block 606 to select another platform 304 (and/or subplatform 306). When there are no additional platforms 304 (and/or subplatforms 306) to be analyzed (block 610), the example platform selector 124 of FIG. 1 selects a desired number of highest performance per unit cost platforms (and/or subplatforms) (block 612). For example, the platform selector 124 may select a set of platforms 304 (and/or subplatforms 306) on which an advertising campaign may be most effectively implemented. The selected set of platforms 304 (and/or subplatforms 306) may be output as a recommendation or selection for informing the advertising campaign. In some examples, the platform selector 124 selects and/or outputs the recommendation or selection of platforms 304 and/or subplatforms 306 to compensate for overlapping audiences (e.g., based on overlap information). The example instructions 600 of FIG. 6 then end.

FIG. 7 is a flowchart representative of example computer readable instructions 700 which, when executed, cause a computer to implement the example system 100 of FIG. 1 to estimate performance of a campaign. The example instructions 700 of FIG. 7 may be executed to implement the example audience measurement systems 102, 108-118, the example effectiveness determiner 104, the example platform metric calculator 106, and/or the example performance estimator 120 of FIG. 1.

The example performance estimator 120 of FIG. 1 obtains (e.g., receives, accesses from storage) effectiveness metrics for platforms of an advertising campaign (e.g., the example platform metrics 406 for the example platforms 304 of FIG. 4, the media impact performance metric $I_P$ of equation (3)) (block 702). For example, the performance estimator 120 may receive a description of an advertising campaign (e.g., a listing of platforms 304 and/or subplatforms 306) and request effectiveness metrics (e.g., the example effectiveness metrics 310 of FIG. 3) of the described platforms (e.g., from the effectiveness determiner 104 of FIG. 1). The example performance estimator 120 obtains (e.g., receives, accesses from storage) reach (e.g., the example reach 312 of FIG. 3, the reach $R_P$ of equation (2)) for the platforms of the advertising campaign (block 704). For example, the performance estimator 120 requests reach 312 for each of the described platforms 304 from the audience measurement system 102 and/or from the platform-specific audience measurement systems 108-118.

The example performance estimator 120 selects a first platform 304 of the advertising campaign (block 706). The performance estimator 120 calculates a platform metric (e.g., a performance metric 314, the total platform performance $TP_P$ of equation (4)) for the selected platform 304 based on the effectiveness metric 310 and the reach 312 (block 708). The platform metric 314 therefore represents an estimate of the performance of the platform 304 (e.g., an estimate of the performance of a portion of the advertising campaign). The performance estimator 120 determines whether there are additional platforms 304 in the advertising campaign to be analyzed (block 710) and, if so, returns to block 706 to select another platform 304 to be analyzed.

When there are no further platforms 304 to be analyzed (block 710), the example performance estimator 120 sums the platform metrics 304 of the platforms of the advertising campaign to estimate the overall performance of the campaign (e.g., the campaign performance 410 of FIG. 4) (block 712). For example, by summing the platform metrics 314 (that represent the individual platforms) for all platforms 304 that are used in the campaign, the example performance estimator 120 may estimate a total or overall performance 410 of the campaign (e.g., the estimated performance of the campaign $P_{campaign}$). In some examples, the performance 410 for the campaign represents an estimated number of people affected or influenced by the campaign, where a higher performance affects more people.

The example performance estimator 120 determines whether there are changes to the ad campaign (block 714). If there are changes (block 714), control returns to block 702 to calculate a performance of the modified campaign. If there are no changes (block 714), the example instructions 700 end.

Figure 8:
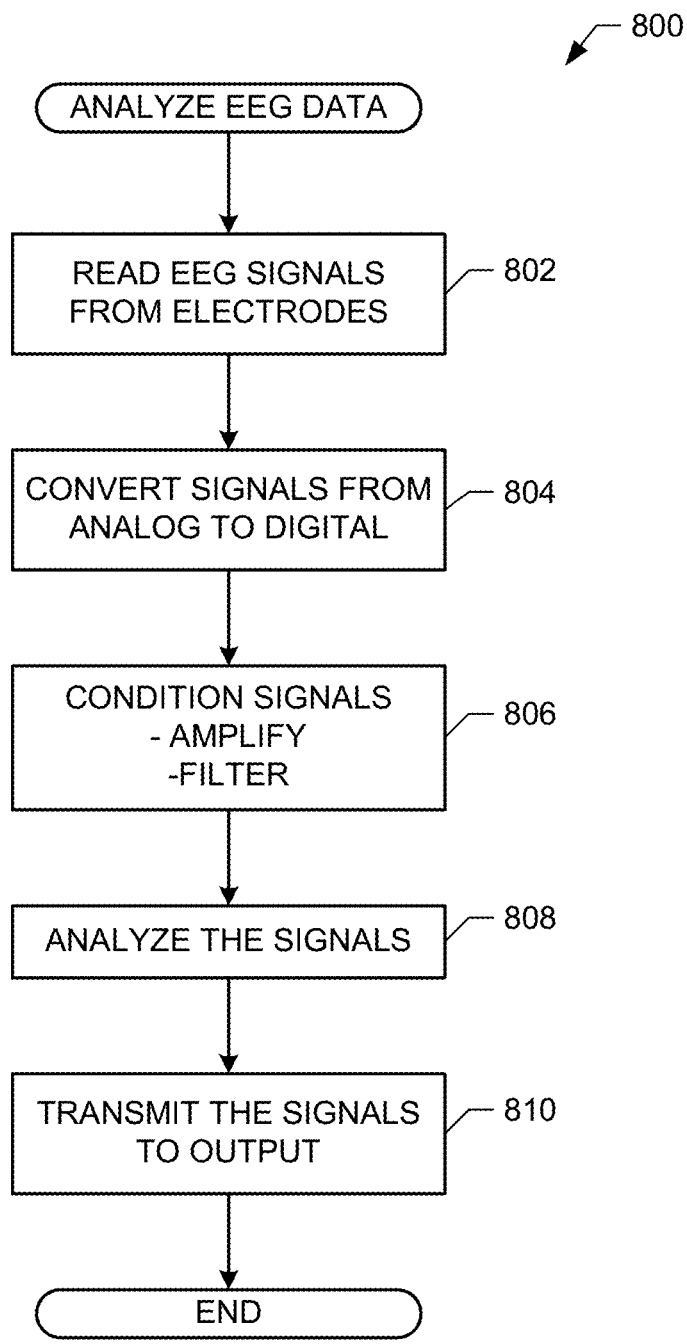
FIG. 8 is a flowchart representative of example computer readable instructions which may be executed to analyze EEG data collected from the example headset and implemented by the example effectiveness determiner of FIG. 2.

FIG. 8 is a flowchart illustrating example machine readable instructions 800 which may be executed to analyze EEG data collected from the example headset 202 and implemented by the example effectiveness determiner 104 of FIG. 2. The example headset 202 has a plurality of electrodes that contact the scalp of a subject to receive electrical signals from the subject's brain. The example instructions 800 for analyzing EEG data includes reading the EEG signals from the electrodes of the EEG sensor 204 (block 802). In the illustrated example, the signals are converted from an analog signal to a digital signal (block 804). In some examples, the analog-to-digital conversion takes place in a processing unit, such as, for example, a remote processor for example at the example remote data facility 220. In other examples, the analog-to-digital conversion takes place adjacent the electrodes within the headset 202 to convert the signal as close to the source as possible.

In the illustrated example, the signals are conditioned (block 806) to improve the usefulness of the signals and the accessibility of the data contained therein. For example, the conditioning may include amplifying the signals and/or filtering the signals (e.g., with a band pass filter).

The signals are analyzed (block 808) to, for example, determine a mental state of the subject, an engagement with media as an audience member, and/or otherwise in accordance with the teachings of this disclosure. For example, the signals may be analyzed by the attention evaluator 812 as disclosed above to determine and/or calculate region(s) of brain activity, interaction(s) between regions of brain activity, frequency interaction(s), frequency coupling(s), inter-regional coherencies of frequency band, gain(s), phase(s), inter-hemispheric measurement(s), asymmetry in one or more frequency band(s), inter-hemispheric asymmetry, asymmetry in inter-regional intra-hemispheric coherence, asymmetry in inter-regional intra-hemispheric inter-frequency coupling, pattern(s) of oscillation in frequency band(s), degree(s) of phase synchrony between oscillation patterns, repeating sequence(s) of relative phase angles between oscillation patterns, amplitude difference(s) and/or other calculations.

In the illustrated example, the signals are transmitted to an output (block 810), such as, for example, by the transmitter 216 of the example effectiveness determiner 104. In addition, the output may include the wired or wireless communications detailed herein. After the output (block 810), the example instructions 800 ends.

Figure 9:
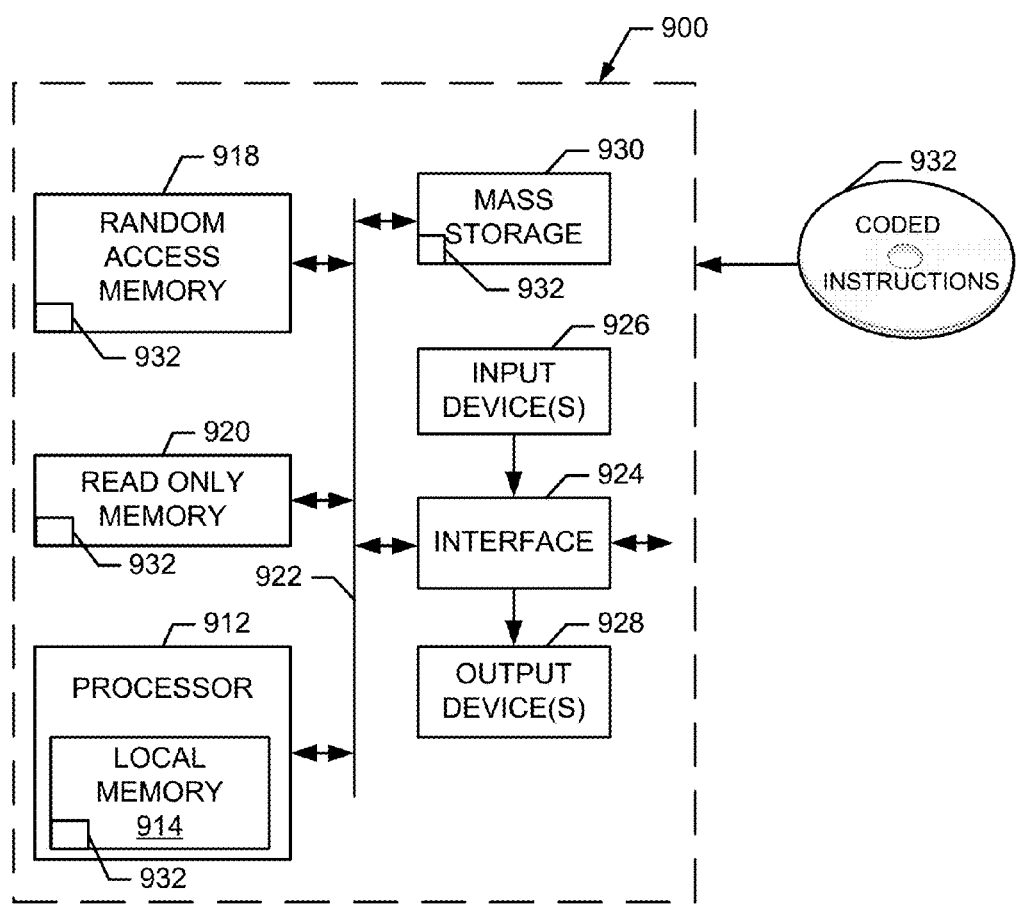
FIG. 9 is a block diagram of an example processor platform capable of executing the instructions of FIGS. 5, 6, 7, and/or 8 to implement the systems of FIGS. 1 and/or 2.

FIG. 9 is a block diagram of an example processor platform 900 capable of executing the instructions of FIGS. 5, 6, 7, and/or 8 to implement the system 100 of FIGS. 1 and/or 2. The processor platform 900 can be, for example, a server, a personal computer, a mobile device (e.g., a cell phone, a smart phone, a tablet such as an iPad™), or any other type of computing device.

The processor platform 900 of the illustrated example includes a processor 912. The processor 912 of the illustrated example is hardware. For example, the processor 912 can be implemented by one or more integrated circuits, logic circuits, microprocessors or controllers from any desired family or manufacturer.

The processor 912 of the illustrated example includes a local memory 913 (e.g., a cache). The processor 912 of the illustrated example is in communication with a main memory including a volatile memory 914 and a non-volatile memory 916 via a bus 918. The volatile memory 914 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 916 may be implemented by flash memory and/or any other desired type of memory device. Access to the main memory 914, 916 is controlled by a memory controller.

The processor platform 900 of the illustrated example also includes an interface circuit 920. The interface circuit 920 may be implemented by any type of interface standard, such as an Ethernet interface, a universal serial bus (USB), and/or a PCI express interface.

In the illustrated example, one or more input devices 922 are connected to the interface circuit 920. The input device(s) 922 permit(s) a user to enter data and commands into the processor 912. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 924 are also connected to the interface circuit 920 of the illustrated example. The output devices 924 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 920 of the illustrated example, thus, typically includes a graphics driver card, a graphics driver chip or a graphics driver processor.

The interface circuit 920 of the illustrated example also includes a communication device such as a transmitter, a receiver, a transceiver, a modem and/or network interface card to facilitate exchange of data with external machines (e.g., computing devices of any kind) via a network 926 (e.g., an Ethernet connection, a digital subscriber line (DSL), a telephone line, coaxial cable, a cellular telephone system, etc.).

The processor platform 900 of the illustrated example also includes one or more mass storage devices 928 for storing software and/or data. Examples of such mass storage devices 928 include floppy disk drives, hard drive disks, compact disk drives, Blu-ray disk drives, RAID systems, and digital versatile disk (DVD) drives.

The coded instructions 932 of FIGS. 5, 6, 7, and/or 8 may be stored in the mass storage device 928, in the volatile memory 914, in the non-volatile memory 916, and/or on a removable tangible computer readable storage medium such as a CD or DVD.

Methods and apparatus disclosed herein advantageously enable rationalization and/or comparison of media campaigns and/or ratings across different media platforms. Example methods and apparatus disclosed herein enable the estimation and/or prediction of performance of a media campaign and/or can be used to improve or even optimize cross-platform campaigns (e.g., optimization of expenditures between different media platforms), thereby increasing return-on-investment for advertisers.

Example methods and apparatus disclosed herein use a media impact performance metric to take into account the differing levels of engagement, attention and, more generally, effectiveness or efficiency of different media platforms. Example methods and apparatus disclosed herein further use the media impact performance metric to compare different media platforms to, for example, determine an improved (e.g., optimal) mix of platforms on which to advertise to make efficient and effective use of an advertising campaign budget.

To the extent any of the documents incorporated by reference herein conflict with this disclosure, this disclosure is considered to control.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus, comprising:
  a sensor to measure first neuro-response data from a person when exposed to media output via a first media delivery platform type, the sensor to measure second neuro-response data from the person when exposed to media output via a second media delivery platform type, the first media delivery platform type being different than the second media delivery platform type;
  a performance estimator to:
    calculate a first performance metric based on a first reach of the first media delivery platform type with respect to a target group of audience members and a first effectiveness metric for the first media delivery platform type, the first effectiveness metric based on the first neuro-response data; and
    calculate a second performance metric based on a second reach of the second media delivery platform type with respect to the target group of audience members and a second effectiveness metric for the second media delivery platform type, the second effectiveness metric based on the second neuro-response data; and
  a platform selector to rate at least one of the first media delivery platform type or the second media delivery platform type based on the first and the second performance metrics, at least one of the performance estimator, the sensor or the platform selector including hardware.

2. The apparatus as defined in claim 1, further including a performance per unit cost estimator to:
  access a first ad campaign cost for the first media delivery platform type and a second ad campaign cost for the second media delivery platform type;
  calculate a first platform performance per unit cost for the first media delivery platform type based on the first performance metric and the first ad campaign cost; and
  calculate a second platform performance per unit cost for the second media delivery platform type based on the second performance metric and the second ad campaign cost; and
  wherein the platform selector is further to select the first media delivery platform type or the second media delivery platform type for an ad campaign based on the first platform performance per unit cost and the second platform performance per unit cost.

3. The apparatus as defined in claim 1, wherein the person is representative of the target group.

4. The apparatus as defined in claim 1, wherein the first effectiveness metric measures at least one of: engagement, attention, memory, persuasion, effectiveness, emotion, or purchase intent.

5. The apparatus as defined in claim 1, wherein the performance estimator estimates a total performance of a media campaign based on the first and second performance metrics.

6. The apparatus as defined in claim 1, wherein the first media delivery platform type is one of a television platform, a mobile platform, an online platform, an outdoor platform, a radio platform or a print media platform.

7. The apparatus as defined in claim 1, wherein the first performance metric includes a product of the first effectiveness metric and the first reach.

8. A tangible computer readable storage medium comprising computer readable instructions which, when executed by a processor, cause the processor to at least:
measure, with a sensor, first neuro-response data from a person when exposed to media output via a first media delivery platform type, measure, with the sensor, second neuro-response data from the person when exposed to media output via a second media delivery platform type, the first media delivery platform type being different than the second media delivery platform type;
calculate a first performance metric based on a first reach of the first media delivery platform type with respect to a target group of audience members and a first effectiveness metric for the first media delivery platform type, the first effectiveness metric based on the first neuro-response data; and
calculate a second performance metric based on a second reach of the second media delivery platform type with respect to the target group of audience members and a second effectiveness metric for the second media delivery platform type, the second effectiveness metric based on the second neuro-response data; and
rate at least one of the first media delivery platform type or the second media delivery platform type based on the first and the second performance metrics.

9. The tangible computer readable storage medium as defined in claim 8, wherein the instructions cause the processor to:
access a first ad campaign cost for the first media delivery platform type and a second ad campaign cost for the second media delivery platform type;
calculate a first platform performance per unit cost for the first media delivery platform type based on the first performance metric and the first ad campaign cost; and
calculate a second platform performance per unit cost for the second media delivery platform type based on the second performance metric and the second ad campaign cost; and
select the first media delivery platform type or the second media delivery platform type for an ad campaign based on the first platform performance per unit cost and the second platform performance per unit cost.

10. The tangible computer readable storage medium as defined in claim 8, wherein the person is representative of the target group.

11. The tangible computer readable storage medium as defined in claim 8, wherein the first effectiveness metric measures at least one of: engagement, attention, memory, persuasion, effectiveness, emotion, or purchase intent.

12. The tangible computer readable storage medium as defined in claim 8, wherein the instructions cause the processor to estimate a total performance of a media campaign based on the first and second performance metrics.

13. The tangible computer readable storage medium as defined in claim 8, wherein the first media delivery platform type is one of a television platform, a mobile platform, an online platform, an outdoor platform, a radio platform or a print media platform.

14. The tangible computer readable storage medium as defined in claim 8, wherein the first performance metric includes a product of the first effectiveness metric and the first reach.

15. A method, comprising:
measuring, with a sensor, first neuro-response data from a person when exposed to media output via a first media delivery platform type;
measuring, with the sensor, second neuro-response data from the person when exposed to media output via a second media delivery platform type, the first media delivery platform type being different than the second media delivery platform type;
accessing, by executing an instruction with a processor, a first performance metric for the first media delivery platform type and a second performance metric for the second media delivery platform type, the first performance metric based on a first reach of the first media delivery platform type with respect to a target group of audience members and a first effectiveness metric for the first media delivery platform type, the first effectiveness metric based on the first neuro-response data, the second performance metric based on a second reach of the second media delivery platform type with respect to the target group and a second effectiveness metric for the second media delivery platform type, the second effectiveness metric based on the second neuro-response data; and
rating, by executing an instruction with the processor, at least one of the first media delivery platform type or the second media delivery platform type based on the first and the second platform metrics.

16. The method as defined in claim 15, further including:
accessing, by executing an instruction with the processor, a first ad campaign cost for the first media delivery platform type and a second ad campaign cost for the second media delivery platform type;
calculating, by executing an instruction with the processor, a first platform performance per unit cost for the first media delivery platform type based on the first performance metric and the first ad campaign cost;
calculating, by executing an instruction with the processor, a second platform performance per unit cost for the second media delivery platform type based on the second performance metric and the second ad campaign cost;
selecting, by executing an instruction with the processor, the first media delivery platform type or the second media delivery platform type for an ad campaign based on the first platform performance per unit cost and the second platform performance per unit cost.

17. The method as defined in claim 15, wherein the person is representative of the target group.

18. The method as defined in claim 15, wherein the first effectiveness metric measures at least one of: engagement, attention, memory, persuasion, effectiveness, emotion, or purchase intent.

19. The method as defined in claim 15, further including estimating, by executing an instruction with the processor, a total performance of a media campaign based on the first and second performance metrics.

20. The method as defined in claim 15, wherein the first media delivery platform type is one of a television platform, a mobile platform, an online platform, an outdoor platform, a radio platform or a print media platform.

* * * * *